United States Patent
Yamaguchi et al.

(10) Patent No.: US 6,770,777 B2
(45) Date of Patent: Aug. 3, 2004

(54) PROCESS FOR PRODUCING 2-ALKYL-2-ADAMANTYL ESTER

(75) Inventors: Masao Yamaguchi, Yamaguchi (JP); Hideki Kikuchi, Yamaguchi (JP); Yoshihiro Hirota, Yamaguchi (JP)

(73) Assignee: Tokuyama Corporation, Tokuyama (JP)

(*) Notice: Subject to any disclaimer, the term of this patent is extended or adjusted under 35 U.S.C. 154(b) by 0 days.

(21) Appl. No.: 10/276,690

(22) PCT Filed: May 15, 2001

(86) PCT No.: PCT/JP01/04028
§ 371 (c)(1),
(2), (4) Date: Nov. 18, 2002

(87) PCT Pub. No.: WO01/87817
PCT Pub. Date: Nov. 22, 2001

(65) Prior Publication Data
US 2003/0120106 A1 Jun. 26, 2003

(30) Foreign Application Priority Data
May 16, 2000 (JP) ......................... 2000-143036

(51) Int. Cl.⁷ .............................................. C07C 69/52
(52) U.S. Cl. ..................................................... 560/220
(58) Field of Search .......................................... 560/220

(56) References Cited

U.S. PATENT DOCUMENTS 6,945,306 * 12/2002 Uretani et al.

FOREIGN PATENT DOCUMENTS

JP      10-182552      7/1998

OTHER PUBLICATIONS

M. -Y. Kuo et al.: "One–pot preparation of tertiary alkyl carboxylates and sulfonates from ketones" J. Org. Chem., vol. 52, No. 13, pp. 2927–2929 1987.
P.J. Pearce et al.: "A one–step alternative to the grignard reaction" J. Chem. Soc., PERKIN TRANS. (I), pp. 1655–1660 1972.

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

This invention discloses a process for preparing an 2-alkyl-2-adamantyl ester comprising the steps of combining a solution or suspension of 2-adamantanone and an alkyl halide with lithium metal for reacting them to generate an lithium 2-alkyl-2-adamantyl alcoholate, and then reacting the lithium 2-alkyl-2-adamantyl alcoholate with an acid halide.

4 Claims, No Drawings

PROCESS FOR PRODUCING 2-ALKYL-2-ADAMANTYL ESTER

This application is a 321 of PCT/JP01/040278 file May 15, 2001.

TECHNICAL FIELD

This invention relates to a process for preparing an 2-alkyl-2-adamantyl ester such as 2-alkyl-2-adamantyl acrylates and 2-alkyl-2-adamantyl methacrylates (hereinafter, collectively referred to as 2-alkyl-2-adamantyl (meth) acrylates), which are useful as a material for producing a semiconductor resist.

BACKGROUND OF THE INVENTION

A resist prepared from an 2-alkyl-2-adamantyl ester as a starting material has been known to be highly resistant to dry etching during a process for producing a semiconductor (see, e.g., JP-A 5-265212), and has been thus expected to be a promising resist for a semiconductor.

A known process for preparing an 2-alkyl-2-adamantyl ester involves alkylating 2-adamantanone using an alkylating agent consisting of an organometallic compound, and then esterifying the resulting metal 2-alkyl-2-adamantyl alcoholate with an acid halide (e.g., JP-A 10-182552).

In the first alkylation step in the above reaction, when the alkylating reagent is an organomagnesium or organoaluminum compound, a reduction reaction preferentially proceeds, leading to a reduced yield of the alkyl compound as described in, e.g., Tetrahedron Lett., Vol. 31 (22), p. 3151 (1990). Thus, a desired ester may be obtained in a significantly lower yield.

For example, as described in Comparative Examples later, selectivities for an alkylated product (an ethylated compound) and a reduced product (2-adamantanol) were 25% and 75%, respectively, in a reaction of 2-adamantanone with ethylmagnesium iodide. As a result, a reaction yield of the ester was significantly low, i.e., about 20% based on 2-adamantanone. In the reaction, a lower content of the ester makes its purification very difficult. Thus, the ester with a high purity cannot be obtained using a common purification method.

In general, alkylation using an alkyllithium as an alkylating reagent may frequently eliminate a reduction reaction as described above, allowing the above problem to be solved. An alkyllithium itself may be, however, prepared in a lower yield and has a short half life as indicated in J. Am. Chem. Soc., Vol. 63, p. 2480 (1941) describing that ethyl lithium is prepared from ethyl bromide and lithium metal in an yield of at most about 50%, and in "Yuki Kagaku Jikken No Tebiki (Guide for Organic Chemical Experiments), Kagaku Dojin, p. 34 (1988) describing that ethyl lithium has a half life as short as 54 hours. Thus, the reagent is expensive and unstable.

Alkylation with an alkyllithium is, therefore, not unfavorable due to its higher production cost and troublesome operation in the light of the overall production process. Thus, the yield in the first alkylation step also significantly affects the yield of the ester.

On the other hand, there have been known the conditions under which the second esterification step may stoichiometrically proceed, particularly when the metal is lithium. However, when using acryloyl chloride or methacryloyl chloride (hereinafter, acrylic and methacrylic acids are collectively referred to as (meth)acrylic acid) as an acid halide for esterification of a metal 2-alkyl-2-adamantyl alcoholate prepared by alkylation of 2-adamantanone, an ester produced is polymerized during the reaction, resulting in a reduced overall yield.

A resist material for a semiconductor must be highly pure. Conventional processes for preparing an 2-alkyl-2-adamantyl ester, therefore, carry industrially serious problems in terms of a lower yield and difficulty in purification.

SUMMARY OF THE INVENTION

We have extensively investigated processes for preparing an 2-alkyl-2-adamantyl (meth)acrylate by reacting lithium 2-alkyl-2-adamantyl alcoholate with (meth)acryloyl chloride, and have found that an —OLi group in an lithium 2-alkyl-2-adamantyl alcoholate polymerizes 2-alkyl-2-adamantyl (meth)acrylate produced by the reaction.

In addition, we have found that when a solution of lithium 2-alkyl-2-adamantyl alcoholate is added to (meth)acryloyl chloride, polymerization of the 2-alkyl-2-adamantyl(meth) acrylate can be prevented.

Furthermore, we have intensely investigated alkylation of 2-adamantanone and have found that 2-adamantanone can be alkylated by reacting 2-adamantanone, lithium metal and an alkyl halide instead of using an unstable alkyllithium described above. We have also found that a solution containing 2-adamantanone and alkyl halide can be slowly added to lithium metal to alkylate 2-adamantanone more effectively, and that the alkylation reaction gives a highly pure product and thus a resulting solution can be directly used in the subsequent esterification without further isolation to give a highly pure product after isolation. Thus, this invention has been achieved on the basis of these findings.

Thus, an objective of this invention is to provide a process for preparing an 2-alkyl-2-adamantyl ester with a high purity in an improved yield from 2-adamantanone without using an expensive and unstable compound such as an alkyl lithium.

Another objective of this invention is to provide a process for preparing an 2-alkyl-2-adamantyl ester whereby the ester can be produced in a high yield by preventing the ester from polymerizing during esterification of a metal 2-alkyl-2-adamantyl alcoholate with an acid halide.

For realizing the above objectives, this invention provides:

[1] A process for preparing an 2-alkyl-2-adamantyl (meth) acrylate comprising the step of adding a solution of a lithium 2-alkyl-2-adamantyl alcoholate to a (meth) acryloyl halide to react the lithium 2-alkyl-2-adamantyl alcoholate with the (meth)acryloyl halide.

[2] The process for preparing an 2-alkyl-2-adamantyl (meth)acrylate as described in [1] wherein the solution of the lithium 2-alkyl-2-adamantyl alcoholate is prepared by combining a solution or suspension containing 2-adamantanone and an alkyl halide with lithium metal.

[3] The process for preparing an 2-alkyl-2-adamantyl (meth)acrylate as described in [1] wherein the alkyl is alkyl having 1 to 6 carbon atoms.

[4] The process for preparing an 2-alkyl-2-adamantyl (meth)acrylate as described in [1] wherein the alkyl is ethyl.

In this invention, a solution or suspension of 2-adamantanone and an alkyl halide is reacted with lithium metal to prepare a solution of an lithium 2-alkyl-2-adamantyl alcoholate. The lithium 2-alkyl-2-adamantyl alcoholate can be, therefore, prepared in a high yield and furthermore, the resulting alcoholate is reacted with an acid halide to give a desired product, an 2-alkyl-2-adamantyl ester in a high yield.

The lithium 2-alkyl-2-adamantyl alcoholate can be prepared in a high yield when a solution or suspension of 2-adamantanone and an alkyl halide is added to lithium metal. Furthermore, when the solution of the lithium 2-alkyl-2-adamantyl alcoholate thus prepared is added to an esterifying agent or its solution, the desired product, 2-alkyl-2-adamantyl (meth)acrylate, is prevented from polymerizing. As a result, the yield of the desired product is improved. Furthermore, a reduced amount of impurities in the desired product makes a purification process easier and thus the desired product can be obtained easier with a high purity.

According to the preparation process of this invention, a desired product can be obtained in a higher yield than a process using a Grignard reagent. In addition, since the process does not use an alkyllithium which must be separately prepared and is unstable, an adamantyl ester can be easily prepared with a lower cost.

BEST MODE FOR CARRYING OUT THE INVENTION

Preparation of a Lithium 2-alkyl-2-adamantyl Alcoholate

As described above, in the first step of the process according to this invention, a solution or suspension of 2-adamantanone represented by formula (1) and an alkyl halide represented by formula (2):

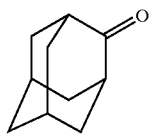

(1)

R¹–X (2)

wherein R represents alkyl having 1 to 6 carbon atoms and X represents halogen, is combined with lithium metal for initiating alkylation of 2-adamantanone to prepare a lithium 2-alkyl-2-adamantyl alcoholate represented by formula (3):

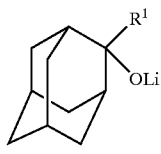

(3)

wherein $R^1$ represents alkyl having 1 to 6 carbon atoms.

One starting material, 2-adamantanone is commercially available as a reagent or industrial grade, which may be used as it is or after purification by, for example, recrystallization or sublimation.

The other starting material, an alkyl halide (2), may be selected from, but not limited to, alkyl bromides, alkyl iodides and alkyl chlorides. In the light of availability of the starting material, preferred are alkyl bromides and iodides having 1 to 6 carbon atoms. Specific examples include butyl chloride, pentyl chloride, hexyl chloride, methyl bromide, ethyl bromide, butyl bromide, methyl iodide and ethyl iodide.

The amount of the alkyl halide is desirably 2-adamantanone:alkyl halide=1:1 to 1:1.2 in a molar ratio, taking a high conversion rate of 2-adamantanone into account.

A solvent or dispersion medium which dissolves or disperses 2-adamantanone and the alkyl halide may be an organic solvent which is stable to lithium metal, an alkyllithium and a lithium alcoholate. Examples of such an organic solvent include ethers such as diethyl ether, dioxane and tetrahydrofuran; hydrocarbons such as hexane and toluene; and mixtures thereof.

Such an organic solvent is preferably used in an amount such that the concentration of 2-adamantanone is 0.01 to 10 mol/L, particularly 0.1 to 5 mol/L in the light of a crude yield, solubility and a reaction rate, but not limited to the range.

The total amount of lithium metal is preferably, but not limited to, 1.6 to 2.4 gram atom, particularly 1.8 to 2.2 gram atom per 1 mole of adamantanone in the light of an yield and avoiding excessive use of lithium metal.

When subsequently conducting the esterification reaction described below, it is preferable that lithium metal in the reaction solution and the alkyllithium generated in the reaction system are substantially absent after the alkylation. The amount of lithium metal is, therefore, preferably 2 gram atom or less, particularly 1.8 to 2.0 gram atom per 1 mole of 2-adamantanone.

There are no restrictions to a procedure of the reaction initiated by combining a solution or suspension (an organic material mixture) of 2-adamantanone and an alkyl halide with lithium metal. Specifically, in terms of the order of addition, the organic material mixture may be added to lithium metal or lithium metal may be added to the organic material mixture. In terms of a mixing procedure, these materials may be mixed together at a time, successively or continuously.

Among these mixing procedures, addition of an organic material mixture to lithium metal is particularly preferable because it can prevent lithium metal from being inactivated, increase a reaction rate and prevent lithium metal from remaining at the end of the reaction. In the procedure, to lithium metal is added an organic material mixture portionwise over a relatively longer period, or dropwise continuously or intermittently while controlling a reaction temperature within the range described later.

In contrast, when adding lithium metal portionwise to an organic material mixture, a time for activating a metal surface is required after adding each aliquot of lithium metal. Thus, the overall reaction proceeds in a lower rate. However, in the mixing procedure of adding the organic material mixture to lithium metal, the whole amount of lithium metal used can be activated during an initial stage of the reaction so that the reaction may be quite smooth.

A time for adding the organic material mixture to lithium metal may vary depending on a production scale, but is preferably 0.5 to 48 hours.

Lithium metal may be used preferably as granules, foils or particles having a large surface area which can accelerate the reaction.

A rate of adding the organic material mixture cannot be particularly defined because it varies depending on the type of an alkyl halide used. Generally, it is desirable to adjust an addition rate such that a reaction temperature does not exceed a lower temperature of a boiling point of the alkyl halide or a boiling point of the organic solvent used.

In particular, when the alkyl halide is an iodide, it is desirable to add an organic material mixture while maintaining a reaction temperature to 0° C. or lower in the light of minimizing side reactions. When the alkyl halide is a bromide, it is desirable to add an organic material mixture to lithium metal while maintaining a reaction temperature to a level not only meeting the above conditions but also equal to or exceeding 20° C., that is, 20° C. to a lower tempeature of a boiling point of the alkyl halide or a boiling point of the organic solvent used. Conducting such adjustment may prevent inactivation of lithium metal. During adding the organic material mixture is preferably added to lithium while stirring the solvent.

A reaction time for the above alkylation may vary depending on factors such as the amount of lithium metal used and a cooling efficiency, but is preferably 0.5 to 10 hours after adding an organic material mixture. The reaction is desirably conducted in an inert atmosphere such as argon for preventing inactivation of lithium metal.

Esterification

In the process for preparing an 2-alkyl-2-adamantyl ester according to this invention, an 2-alkyl-2-adamantyl alcoholate prepared by the above alkylation is reacted with an acid halide to prepare the 2-alkyl-2-adamantyl ester.

One starting material in the esterification, an 2-alkyl-2-adamantyl alcohol may be used as a lithium 2-alkyl-2-adamantyl alcoholate as prepared above without being isolated. Alternatively, a lithium 2-alkyl-2-adamantyl alcoholate may be separated and if necessary purified before being used in a subsequent reaction.

When separating the lithium 2-alkyl-2-adamantyl alcoholate from a reaction solution, the lithium 2-alkyl-2-adamantyl alcoholate itself may be not necessarily isolated. If possible, the above alcoholate may be separated from the remaining lithium metal while being dissolved in the solution. When the reaction solution after the above alkylation does not substantially contain lithium metal, the reaction solution may be used directly as a material for esterification.

If the reaction solution is used as a material for esterification while containing lithium metal or an alkyllithium remains in a large amount, it may cause inactivation of an acid halide or polymerization of an 2-alkyladamantyl ester produced, leading to reduction in an yield of the desired 2-alkyladamantyl ester.

An acid halide of the other starting material used in the esterification is not limited as long as it corresponds to the structure of a desired product. Halogens which can be shown include chlorine, bromine and iodine. Chlorine is preferable because it can readily prepare an acid halide.

Examples of an acid halide which can be used in the esterification include acetyl chloride, acetyl bromide, acryloyl chloride, methacryloyl chloride, benzoyl chloride and 4-vinylbenzoyl chloride.

Among these, an acryloyl or methacryloyl halide, particularly acryloyl or methacryloyl chloride, is preferable as a starting material for an alkyladamantyl ester which is very useful as a resist.

In the esterification, the amount of a lithium 2-alkyl-2-adamantyl alcoholate and an acid halide is preferably 0.9 to 2.0 moles of an acid halide per 1 mole of a lithium 2-alkyl-2-adamantyl alcoholate, more preferably 1.0 to 1.3 moles because an yield may be improved.

The above esterification may be initiated by contacting the lithium 2-alkyl-2-adamantyl alcoholate with the acid halide in a solvent.

Any solvent may be used as long as it does not react with an alcoholate or an esterifying agent. Examples of such a solvent include ethers such as ethyl ether, tetrahydrofuran (THF) and dioxane; and hydrocarbons such as hexane, toluene and xylenes.

A concentration of an lithium 2-alkyl-2-adamantyl alcoholate in the above solvent is preferably 0.01 to 10 mol/L, more preferably 0.1 to 1 mol/L in the light of handling.

There are no restrictions to a procedure of contacting a lithium 2-alkyl-2-adamantyl alcoholate with an acid halide in a solvent. They may be combined by adding a lithium 2-alkyl-2-adamantyl alcoholate (or its solution) and an acid halide (or its solution) simultaneously and separately to a solvent; by adding an acid halide (or its solution) to a solution of a lithium 2-alkyl-2-adamantyl alcoholate; or by adding a lithium 2-alkyl-2-adamantyl alcoholate (or its solution) to a solution of an acid halide.

A particularly preferable procedure of contacting an lithium 2-alkyl-2-adamantyl alcoholate with an acid halide in a solvent is as follows. A solution of the lithium 2-alkyl-2-adamantyl alcoholate is added to the acid halide or its solution to initiate an esterification reaction by which an 2-alkyl-2-adamantyl (meth)acrylate is produced.

The above contacting procedure can effectively prevent the 2-alkyl-2-adamantyl (meth)acrylate produced during the reaction from polymerizing due to the presence of the —OLi group in the lithium 2-alkyl-2-adamantyl alcoholate, resulting in improvement in an yield of the desired product. Such an effect is particularly prominent when the acid halide is an acryloyl halide or methacryloyl halide.

When adding a solution of the lithium 2-alkyl-2-adamantyl alcoholate to an acid halide or its solution, it may be preferable to continuously or intermittently add dropwise the solution of the lithium 2-alkyl-2-adamantyl alcoholate to the acid halide or its solution over a relatively longer period while maintaining a reaction temperature within the range described below. A dropping period may be, therefore, often about 1 to 48 hours although it depends on a production scale.

Depending on a dropping period, a reaction time is preferably 0.5 to 10 hours after completion of addition.

A reaction temperature in the esterification may not be particularly restricted, but is preferably −20 to 100° C., particularly preferably −20 to 50° C. in the light of balance between a reaction rate and prevention of polymerization.

The reaction is desirably conducted in an atmosphere of an inert gas such as nitrogen and argon for preventing inactivation of an acid halide or a lithium 2-alkyl-2-adamantyl alcoholate.

The reaction system may contain a polymerization inhibitor unreactive to a lithium alkoxide. Examples of such a polymerization inhibitor include those without a phenolic hydroxyl group such as phenothiazine.

Esterification can be conducted as described above to obtain a desired alkyladamantyl ester by using corresponding to an alkyl halide and an acid halide used. For example, when using an alkyl halide comprising alkyl having 1 to 6 carbon atoms as an alkyl halide and an acryloyl or methacryloyl halide as an acid halide, an alkyladamantyl (meth) acrylate represented by formula (4) can be obtained.

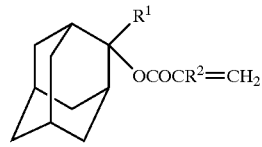

(4)

wherein $R^1$ represents alkyl having 1 to 6 carbon atoms; and $R^2$ represents hydrogen or methyl.

A desired product may be obtained from a reaction solution after esterification, by removing a lithium halide as a byproduct by an appropriate procedure such as washing with water, removing a solvent, and then purifying it by a proper method such as column chromatography, distillation and recrystallization.

EXAMPLES

This invention will be more specifically described with reference to, but not limited to, Examples.

Example 1

In a 500 mL four-necked flask equipped with a stirring blade, a thermometer, a reflux condenser and a dropping funnel were placed 30 g of tetrahydrofuran and 2.78 g (0.4 mol) of lithium metal under a nitrogen atmosphere. To the solution was added dropwise a solution of 30 g (0.2 mol) of 2-adamantanone and 26.2 g (0.24 mol) of ethyl bromide in 90 g of tetrahydrofuran under a nitrogen atmosphere while controlling a reaction temperature at about 40° C. After completion of addition, the mixture was heated to 45° C. and then the reaction was matured for 1 hour.

After visually confirming that lithium metal had disappeared, 4.36 g (0.04 mol) of ethyl bromide was added. Then, the mixture was stirred at 45° C. for additional 1 hour to prepare a solution of lithium 2-ethyl-2-adamantyl alcoholate. A conversion rate of 2-adamantanone was 98% as determined by gas chromatography (GC).

In a nitrogen-purged 500 mL four-necked flask equipped with a stirring blade, a thermometer and a reflux condenser were charged 22.0 g (0.21 mol) of methacryloyl chloride and 0.08 g (0.4 mmol) of phenothiazine as a polymerization inhibitor. To the mixture was added dropwise over 2 hours the solution of lithium 2-ethyl-2-adamantyl alcoholate prepared in the above process under a nitrogen atmosphere while maintaining a reaction temperature below 10° C. After completion of addition, the mixture was stirred below 10° C. for 4 hours for maturing the reaction.

After maturing the reaction, to the mixture were added 10 g of methanol and 16 g of a 10 wt % aqueous solution of sodium hydroxide below 10° C., and the mixture was stirred for 1 hour. The organic phase was separated and washed with a 10 wt % aqueous solution of sodium hydroxide. After evaporating the solvent in vacuo, to the residue was added 150 g of methanol while stirring the solution, precipitation of solid was observed. After stirring at room temperature for further 3 hours, the mixture was filtered to give 0.09 g of a solid. In the process, filtration took about 1 minute.

After evaporating the solvent in vacuo from the filtrate obtained, the residue was dissolved in 150 g of heptane. To the solution was added 10 g of activated charcoal, and the mixture was stirred. Then, the mixture was filtered through a pad of Celite for removing charcoal, and then heptane was evaporated in vacuo. The residue was recrystallized from 25 g of isopropyl alcohol to give 24.6 g of 2-ethyl-2-adamantyl methacrylate (an isolation yield of 49.4% from 2-adamantanone). The crystals were 99.0% pure as determined by GC.

Example 2

In a 500 mL four-necked flask equipped with a stirring blade, a thermometer, a reflux condenser and a dropping funnel, 30 g (0.2 mol) of 2-adamantanone and 26.2 g (0.24 mol) of ethyl bromide were dissolved in 120 g of tetrahydrofuran under a nitrogen atmosphere. To the solution was added 2.78 g of lithium metal (0.4 mol) as five portions (four portions of 0.5 g and the last portion of 0.78 g) under a nitrogen atmosphere while controlling a reaction temperature at about 40° C. After completion of addition, the mixture was heated to 45° C. and then the reaction was matured for 1 hour.

After visually confirming that lithium metal had disappeared, 4.36 g (0.04 mol) of ethyl bromide was added. Then, the mixture was stirred at 45° C. for additional 1 hour to prepare a solution of lithium 2-ethyl-2-adamantyl alcoholate. A conversion rate of 2-adamantanone was 93% as determined by GC.

After processing as described in Example 1, to the residue obtained was added methanol to precipitate 0.09 g of a solid. In the process, filtration took about 1 minute.

Treatment with activated charcoal and recrystallization as described in Example 1 gave 22.8 g of 2-ethyl-2-adamantyl methacrylate (an isolation yield of 46.0% from 2-adamantanone). The crystals were 99.2% pure as determined by GC.

Comparative Example 1

As described in Example 1, a solution of lithium 2-ethyl-2-adamantyl alcoholate was prepared, in which a conversion rate of 2-adamantanone was 98% as determined by GC.

To the solution was added 0.08 g (0.4 mmol) of phenothiazine as a polymerization inhibitor. To the mixture was added dropwise over 2 hours 22.0 g (0.21 mol) of methacryloyl chloride under a nitrogen atmosphere while cooling to maintain a reaction temperature below 10° C. After completion of addition, the reaction was stirred below 10° C. for 4 hours to be matured.

After maturing the reaction, to the reaction solution were added 10 g of methanol and 16 g of a 10 wt % aqueous solution of sodium hydroxide while maintaining a temperature below 10° C., and the mixture was stirred for 1 hour. The organic phase was separated and washed with a 10 wt % aqueous solution of sodium hydroxide. After evaporating the solvent in vacuo, to the residue was added 150 g of methanol to precipitate a sticky oil which adhered to the stirring blade and the flask wall. After stirring at room temperature for further 3 hours, the reaction mixture was filtered to give an oil. The weight of the oil obtained by filtration was 4.4 g. The oil was so sticky that it took 30 min for filtration.

After evaporating the solvent from the filtrate obtained in vacuo, the residue was dissolved in 150 g of heptane. To the solution was added 10 g of activated charcoal, and the mixture was stirred. Then, the mixture was filtered through a pad of Celite for removing charcoal, and then heptane was evaporated in vacuo. The residue was recrystallized from 25 g of isopropyl alcohol to give 21.7 g of 2-ethyl-2-adamantyl methacrylate (an isolation yield of 43.8% from 2-adamantanone). The crystals were 99.1% pure as determined by GC.

Example 3

In a 5000 mL four-necked flask equipped with a stirring blade, a thermometer, a reflux condenser and a dropping funnel, 23.3 g (3.33 gram atom, 1.0 equivalent) of lithium metal was dispersed in 500 mL of tetrahydrofuran under a nitrogen atmosphere, and the dispersion was cooled to −10° C. To the dispersion was added dropwise a solution which had been already prepared by dissolving of 250 g of 2-adamantanone (1.67 mol) and 237 g of methyl iodide (1.67 mol) in 2000 mL of tetrahydrofuran.

During dropping, the system was adequately cooled to maintain a reaction temperature below 0° C. After completion of addition, the reaction was matured at 0° C. for 3 hours.

After visually confirming that lithium metal had disappeared, a solution of lithium 2-methyl-2-adamantyl alcoholate was thus prepared. A conversion rate of 2-adamantanone was 98% as determined by gas chromatography (GC).

In a 5000 mL four-necked flask equipped with a stirring blade, a thermometer and a reflux condenser were charged 500 mL of tetrahydrofuran and 170 g of methacryloyl chloride (1.63 mol), and the mixture was cooled to 0° C. Into the flask was added dropwise the above solution of lithium 2-methyl-2-adamantyl alcoholate while cooling to maintain a reaction temperature below 10° C. After completion of addition, the mixture was stirred at room temperature for 3 hours to mature the reaction.

After maturation, the reaction was stopped by adding 100 mL of a 0.1 wt % solution of sodium hydroxide in methanol, and to the mixture was added 2000 mL of hexane. The organic layer was separated, washed with a 5 wt % aqueous solution of sodium hydroxide and then a 20 wt % saline. To the mixture was added 0.2 g of phenothiazine as a polymerization inhibitor, and then the solvent was evaporated in vacuo. The residue was dissolved in 200 mL of chloroform. The resulting solution was added to 2000 mL of methanol. While stirring the solution, precipitation of a solid was observed. After stirring at room temperature for 3 hours, the mixture was filtered to give 1.0 g of a solid.

After evaporating the solvent from the filtrate in vacuo, the residue was further distilled under a reduced pressure to give 232 g of 2-methyl-2-adamantyl methacrylate (0.99 mol, an isolation yield of 59% from 2-adamantanone).

Example 4

A solution of 2-butyl-2-adamantyl alcoholate was prepared as described in Example 1, replacing 33 g of butyl bromide (0.24 mol) for ethyl bromide, and it was reacted with methacryloyl chloride as described in Example 1. After maturing the reaction, to the reaction solution were added 10 g of methanol and 16 g of a 10 wt % aqueous solution of sodium hydroxide while maintaining a temperature below 10° C. After stirring for 1 hour, the organic layer was separated. The organic layer was washed with a 10 wt % aqueous solution of sodium hydroxide.

After evaporating the solvent in vacuo, the residue was further distilled under a reduced pressure to give 22 g of 2-butyl-2-adamantyl methacrylate (an isolation yield of 40% from 2-adamantanone).

Example 5

A reaction was conducted as described in Example 1, replacing 22 g (0.24 mol) of acryloyl chloride for methacryloyl chloride. After maturing the reaction, work-up was conducted as described in Example 1. Distillation under a reduced pressure gave 21 g of 2-ethyl-2-adamantyl acrylate (an isolation yield of 48% from 2-adamantanone).

Example 6

In 2500 mL of tetrahydrofuran was dissolved 250 g (1.67 mol) of 2-adamantanone, and then to the mixture was added 237 g (1.67 mol) of methyl iodide. The solution was cooled to −10° C. While maintaining a temperature below −10° C., lithium metal was added portionwise (initially several portions of 1 g; 23.3 g in total, 3.33 gram atom, 1.0 equivalent). After visually confirming that lithium metal had disappeared, the reaction solution was added to 170 g of methacryloyl chloride (1.63 mol), and the mixture was warmed to room temperature.

Then, after confirming adequate completion of the reaction by GC, the reaction was stopped by adding 100 mL of a 0.1 wt % solution of sodium hydroxide in methanol, and to the mixture was then added 2500 mL of hexane. The organic layer was washed with a 5 wt % aqueous solution of sodium hydroxide and a 20 wt % saline. After adding 0.2 g of phenothiazine as a polymerization inhibitor, the solvent was evaporated in vacuo. The residue was dissolved in 200 mL of chloroform, and the solution was poured into 2000 mL of methanol. The insoluble (22 g) was removed by filtration, and the filtrate was evaporated in vacuo. The residue was further distilled under a reduced pressure to give 200 g of 2-methyl-2-adamantyl methacrylate (0.85 mol, an isolation yield of 51% from 2-adamantanone).

Example 7

In 30 mL of tetrahydrofuran was dissolved 30 g (0.2 mol) of 2-adamantanone, and to the solution was then added 24 g (0.22 mol) of ethyl bromide. While vigorously stirring the solution and maintaining a solution temperature below 30° C., lithium metal was added portionwise (initially, several portions of 0.1 g; 2.5 g in total, 0.36 gram atom, 0.82 equivalent). After visually confirming that lithium metal had disappeared, the reaction solution was added to 21 g (0.2 mol) of methacryloyl chloride.

After confirming completion of the reaction by GC, to the solution were added 30 mL of methanol and 3 mL of a 5 wt % aqueous solution of sodium hydroxide, and then the mixture was stirred at room temperature for 1 hour for stopping the reaction. Then, the organic layer containing a desired product was separated and evaporated in vacuo. To the residue was added 200 mL of hexane, and the solution was washed with a 10% aqueous solution of sodium hydroxide and a 20% saline. After evaporating hexane in vacuo, a crude product was obtained. To the crude product were added 0.3 g of phenothiazine and 3 g of diethylene glycol. The mixture was distilled under a reduced pressure to give 17.3 g of 2-ethyl-2-adamantyl methacrylate (0.07 mol, an isolation yield of 35% from 2-adamantanone) with a purify of 95.3%.

Example-8

In 3500 mL of tetrahydrofuran was dissolved 390 g (2.6 mol) of 2-adamantanone, and to the solution was then added 303 g (2.8 mol) of ethyl bromide. While vigorously stirring the solution and maintaining a temperature below 50° C., lithium metal was added portionwise (initially, several portions of 2 g and then several portions of 5 g; 36 g in total, 5.1 gram atom, 0.98 equivalent). The solution was stirred at room temperature overnight. After confirming that lithium metal had disappeared, to the solution was added 0.05 g of phenothiazine and the resulting solution was added to 279 g (2.7 mol) of methacryloyl chloride.

After confirming completion of the reaction by GC, to the solution were added 10 mL of methanol, 10 mL of a 5 wt % aqueous solution of sodium hydroxide and then 2000 mL of hexane. The mixture was washed with a 5 wt % aqueous solution of sodium hydroxide and a 20 wt % saline. After evaporating the organic solvent in vacuo, to the residue was added 2000 mL of methanol. The insoluble (18 g) was removed by filtration and methanol in the filtrate was evaporated in vacuo. To the residue was added 2000 mL of hexane. The insoluble was removed by filtration and hexane in the filtrate was evaporated in vacuo. To the residue was added a seed crystal of 2-ethyl-2-adamantyl methacrylate. After leaving it overnight, crystals formed were collected by filtration.

The crystals were again dissolved in hexane. To the solution was added 30 g of activated charcoal and then the mixture was stirred. The mixture was filtered through a pad of Celite to remove activated charcoal, and hexane in the filtrate was evaporated in vacuo.

The residue was recrystallized from hexane to give 55 g of 2-ethyl-2-adamantyl methacrylate (0.22 mol, an isolation yield of 8.5% from 2-adamantanone). The crystals were 99.1% pure as determined by GC.

Example 9

In 2500 mL of tetrahydrofuran was dissolved 250 g (1.67 mol) of 2-adamantanone, and to the solution was added 237 g (1.67 mol) of methyl iodide. The solution was cooled to below −10° C. To the solution was added lithium metal (initially several portions of about 1 g; 23.3 g in total, 3.33 gram atom, 1.0 equivalent) while maintaining a temperature below −10° C. by cooling.

After visually confirming that lithium metal had disappeared, to the reaction solution was added 170 g (1.63 mol) of methacryloyl chloride, and the reaction solution was warmed to room temperature.

After confirming adequate completion of the reaction by GC, the reaction was stopped by adding 100 mL of a 0.1% solution of sodium hydroxide in methanol, and then to the mixture was added 2500 mL of hexane. The mixture was then washed with a 5% aqueous solution of sodium hydroxide and a 20% saline. After adding 0.2 g of phenothiazine as a polymerization inhibitor, the solvent was evaporated in vacuo. The residual crude product was dissolved in 200 mL of chloroform. The solution was poured into 2000 mL of methanol. After removing the insoluble (5.1 g), the solvent was evaporated in vacuo. The residue was further distilled under a reduced pressure to give 200 g of 2-methyl-2-adamantyl methacrylate (0.85 mol, an isolation yield of 51% from 2-adamantanone).

Comparative Example 2

To 20 mL of freshly distilled ether was added 0.7 g of lithium metal (0.1 gram atom). To the stirred mixture at room temperature was slowly added dropwise 7.8 g (0.05 mol) of ethyl iodide. The solution gradually began refluxing and was cooled to room temperature after completion of addition. The solution was added dropwise a solution of 2-adamantanone (4 g) in freshly distilled tetrahydrofuran (20 ml), and the mixture was stirred at room temperature.

GC analysis did not detect 2-ethyl-2-adamantanol. If lithium 2-ethyl-2-adamantyl alcoholate was formed, GC would detect 2-ethyl-2-adamantanol. It was thus indicated that lithium 2-ethyl-2-adamantyl alcoholate was not formed in this comparative example.

In this comparative example, the reaction probably did not proceed because an yield of ethyl lithium in the first step was too low. Thus, the reaction would proceed by, for example, increasing an yield of ethyl lithium using an increased amount of lithium metal. However, excessive use of lithium metal is not only undesirable in terms of a cost but also leads to a problem that an excessive lithium must be removed before esterification for avoiding the problems described above.

Comparative Example 3

To 5 mL of ether was added 3.7 g (0.15 gram atom) of magnesium. To the mixture was added dropwise a solution of ethyl iodide (30 g, 0.19 mol) in ether (30 mL). The solution of ethylmagnesium iodide thus prepared was added dropwise to a solution of 2-adamantanone (20 g, 0.13 mol) in tetrahydrofuran (100 ml), and the mixture was stirred at room temperature overnight. GC analysis indicated that reduction products, i.e., 2-adamantanol and 2-ethyl-2-adamantanol were formed in 75% and 25%, respectively.

To the resulting reaction solution was added 15.8 g (0.15 mol) of methacryloyl chloride. Then, the mixture was reacted and purified as described in Example 1 to give 32 of a liquid. GC analysis of the liquid indicated the desired 2-ethyl-2-adamantyl methacrylate with a peak area of 20% and a byproduct 2-adamantyl methacrylate with a peak area of 70%. These compounds, however, could not be substantially isolated from the liquid.

Comparative Example 4

In 200 mL of toluene was dissolved 14 g of 2-adamantanone (0.093 mol). To the mixture at room temperature was added dropwise 100 mL of a 0.95 mol/L solution of triethylaluminum in toluene (0.095 mol). Since GC indicated that the reaction did not proceed, the reaction solution was gradually warmed, during which effervescence was observed from about 20° C. to about 40° C. The mixture was heated to 80° C. and was then stirred for 2 hours. GC analysis indicated only 2-adamantanol, a reduction product of 2-adamantanone. A peak 2-ethyl-2-adamantanol derived from Aluminum 2-ethyl-2-adamantyl alcoholate was not detected.

What is claimed is:

1. A process for preparing an 2-alkyl-2-adamantyl (meth)acrylate comprising the step of adding a solution of a lithium 2-alkyl-2-adamantyl alcoholate to a (meth)acryloyl halide to react the lithium 2-alkyl-2-adamantyl alcoholate with the (meth)acryloyl halide.

2. The process for preparing an 2-alkyl-2-adamantyl (meth)acrylate as claimed in claim 1 wherein the solution of the lithium 2-alkyl-2-adamantyl alcoholate is prepared by combining a solution or suspension containing 2-adamantanone and an alkyl halide with lithium metal.

3. The process for preparing an 2-alkyl-2-adamantyl (meth)acrylate as claimed in claim 1 wherein the alkyl is alkyl having 1 to 6 carbon atoms.

4. The process for preparing an 2-alkyl-2-adamantyl (meth)acrylate as claimed in claim 1 wherein the alkyl is ethyl.

* * * * *